(12) United States Patent
Joshi et al.

(10) Patent No.: US 7,470,267 B2
(45) Date of Patent: Dec. 30, 2008

(54) FLUID DELIVERY DEVICE HAVING AN ELECTROCHEMICAL PUMP WITH AN ANIONIC EXCHANGE MEMBRANE AND ASSOCIATED METHOD

(75) Inventors: Ashok V. Joshi, Salt Lake City, UT (US); Strahinja K. Zecevic, Salt Lake City, UT (US); Sai Bhavaraju, Salt Lake City, UT (US); Felix Theeuwes, Los Altos, CA (US); Jeremy Corwin Wright, Los Altos, CA (US)

(73) Assignee: Microlin, LLC, Salt Lake City, UT (US)

( * ) Notice: Subject to any disclaimer, the term of this patent is extended or adjusted under 35 U.S.C. 154(b) by 961 days.

(21) Appl. No.: 10/137,661

(22) Filed: May 1, 2002

(65) Prior Publication Data
US 2003/0205582 A1    Nov. 6, 2003

(51) Int. Cl.
*A61K 9/22* (2006.01)
(52) U.S. Cl. .................................. 604/892.1
(58) Field of Classification Search .............. 604/892.1, 604/891.1, 890.1
See application file for complete search history.

(56) References Cited

U.S. PATENT DOCUMENTS

| | | | |
|---|---|---|---|
| 2,636,852 A | 4/1953 | Juda et al. | |
| 3,845,770 A | 11/1974 | Theeuwes et al. | |
| 3,894,538 A | 7/1975 | Richter | |
| 3,923,426 A | 12/1975 | Theewes | |
| 4,522,698 A | 6/1985 | Maget | |
| 4,549,947 A | 10/1985 | Inoue et al. | |
| 4,552,561 A | 11/1985 | Eckenhoff et al. | 604/896 |
| 4,593,534 A * | 6/1986 | Bloomfield | 62/201 |
| 4,687,423 A | 8/1987 | Maget et al. | |
| 4,886,514 A * | 12/1989 | Maget | 604/891.1 |
| 4,902,278 A | 2/1990 | Maget et al. | |
| 5,030,216 A | 7/1991 | Theeuwes et al. | |
| 5,167,613 A | 12/1992 | Karami et al. | |
| 5,242,565 A | 9/1993 | Winsel | |
| 5,279,608 A | 1/1994 | Cheikh | |
| 5,312,389 A | 5/1994 | Theeuwes et al. | 604/892.1 |
| 5,707,499 A | 1/1998 | Joshi et al. | |
| 5,744,014 A | 4/1998 | Gordon et al. | |
| 5,746,064 A * | 5/1998 | Tsenter | 62/480 |
| 5,785,688 A * | 7/1998 | Joshi et al. | 604/141 |

(Continued)

OTHER PUBLICATIONS

"Office Action for U.S. Appl. No. 11/173,813, Dated Jan. 9, 2007", 1-13.

(Continued)

*Primary Examiner*—Nicholas D. Lucchesi
*Assistant Examiner*—Laura A. Bouchelle
(74) *Attorney, Agent, or Firm*—David Fonda

(57) ABSTRACT

A fluid delivery device, comprising an electrochemical pump, wherein the pump is capable of transporting water; a pump product chamber, wherein the pump product chamber is capable of retaining water generated from the pump; a displaceable member positioned between the pump product chamber and a reservoir, wherein the displaceable member is controllably displaced upon generation of water from the electrochemical pump; a reservoir, wherein the reservoir is capable of containing a fluid which is delivered upon displacement of the displaceable member; and an housing for containing the pump, the pump product chamber, the displaceable member, and the reservoir.

32 Claims, 4 Drawing Sheets

U.S. PATENT DOCUMENTS

| | | |
|---|---|---|
| 5,788,826 A | 8/1998 | Nyberg |
| 5,891,097 A | 4/1999 | Saito et al. |
| 5,925,030 A | 7/1999 | Gross et al. |
| 5,938,640 A | 8/1999 | Maget et al. |
| 5,951,538 A | 9/1999 | Joshi et al. |
| 6,060,196 A | 5/2000 | Gordon et al. |
| 6,163,720 A | 12/2000 | Gyory et al. |
| 6,287,295 B1 * | 9/2001 | Chen et al. ............... 604/892.1 |
| 6,327,426 B1 | 12/2001 | Joshi et al. |
| 6,450,991 B1 | 9/2002 | Bunt et al. |
| 6,491,684 B1 * | 12/2002 | Joshi et al. ............... 604/892.1 |
| 6,575,961 B2 | 6/2003 | Joshi |
| 6,576,362 B2 * | 6/2003 | Hanlon ........................ 429/34 |
| 6,872,292 B2 | 3/2005 | Theeuwes et al. |
| 2004/0241528 A1 | 12/2004 | Chiao et al. |
| 2006/0052768 A1 | 3/2006 | Joshi et al. |
| 2006/0116641 A1 | 6/2006 | Gordon et al. |

OTHER PUBLICATIONS

"Office Action for U.S. Appl. No. 10/908,804, Dated Jan. 3, 2007", 1-9.

Anderson, Office Action for U.S. Appl. No. 11/173,813 sent Sep. 13, 2007, 1-12.

Greene, International Search Report for PCT/US06/22502 sent May 21, 2007, 1-2.

Greene, Written Opinion for PCT/US06/22502 sent May 21, 2007, 1-3.

Copenheaver, International Search Report for PCT/US06/20570 sent Nov. 22, 2006, 1-2.

Copenheaver, Written Opinion for PCT/US06/20570 sent Nov. 22, 2006, 1-4.

* cited by examiner

FLUID DELIVERY DEVICE HAVING AN ELECTROCHEMICAL PUMP WITH AN ANIONIC EXCHANGE MEMBRANE AND ASSOCIATED METHOD

BACKGROUND OF THE INVENTION

1. Field of the Invention

The present invention relates in general to a fluid delivery device, and more particularly, to a fluid delivery device that includes an electrochemical pump for controllably delivering small volumes of fluid with high precision and accuracy.

2. Background Art

In many situations it is necessary, or, at least, desirable to deliver small amounts of fluids and/or chemical agents over a relatively long period of time. Such fluids may include, among others, medicaments, lubricants, fragrant fluids, and chemical agents. A very common, traditional apparatus for the gradual administration of fluid into the human body is an intravenous administration set in which gravity induced hydrostatic infusion dispenses a fluid from a familiarly suspended bottle or bag above the patient.

Other methods for the gradual administration of fluids have been devised to eliminate the need for suspending the fluid above the patient and thereby provide the patient with greater mobility. Mechanical pump dispensers use various types of mechanical pumps to expel the fluid from a reservoir. Charged reservoir dispensers store a fluid under pressure in a flexible reservoir and then selectively expel that fluid by the force of internal reservoir pressure, the rate of release often being regulated by a plurality of complex valve systems. Pressurized gas dispensers use a pressurized gas to expel the fluid. Osmotic dispensers rely on a solute that exhibits an osmotic pressure gradient against water to dispense the fluid.

While the above-identified fluid administration device types or techniques have become available, there remains a continuing desire for improvements therein. When small quantities of fluids are to be administered continuously over a period of many hours, it is desirable to have a fluid dispenser that is highly accurate and reliable, is sufficiently small and lightweight to be portable, and is convenient and easy to use. Gas generating devices have been developed that are both portable and accurate for dispensing small volumes. These gas-generating methods include galvanic cells and electrolytic cells.

In galvanic gas generating cells, hydrogen or oxygen gas is formed at the cathode or anode, respectively, as a result of a reaction between a metal or metal oxide and an aqueous electrolyte. A galvanic cell is by definition an electrochemical cell that requires no externally applied voltage to drive the electrochemical reactions. Typically, the anode and cathode of the galvanic cell are connected through a resistor that regulates the current passed through the cell, and, in turn, directly regulates the production of gas which exerts a force on a diaphragm or piston—thereby expelling the drug. Joshi et al. have been disclosed a number of delivery systems based on the use of galvanic hydrogen generating cell. Examples of such devices are disclosed in U.S. Pat. Nos. 5,951,538, 5,707, 499, and 5,785,688. In the cells disclosed in these patents, a zinc anode react with an alkaline electrolyte producing zinc oxide and water molecules are reduced on porous carbon electrode producing gaseous hydrogen.

U.S. Pat. Nos. 5,242,565 and 5,925,030 disclose a galvanic oxygen-generating cell that is constructed much like a zinc/air button cell, where a reducible oxide is reduced at the cathode while hydroxyl ions are formed. Hydroxyl ions oxidize at the anode, releasing oxygen.

In contrast to galvanic cells, an electrolytic cell requires an external DC power source to drive the electrochemical reactions. When voltage is applied to the electrodes, the electrolyte gives off a gas that exerts a force on a diaphragm or piston—thus expelling the drug. Three types of electrolytic gas generating cells have been proposed for use in drug delivery devices. A first type is based on water electrolysis requiring an operating voltage over 1.23 V. A second type, also known as oxygen and hydrogen gas pumps, require lower DC voltage than the water electrolysis systems. Both of these first and second cell types utilize an ion exchange polymer membrane. A third type of gas generating electrolytic cell is based on the use of an electrolytically decomposable chemical compound that produces a reduced metal at the cathode, and generates gaseous oxygen by oxidation of water at the anode.

U.S. Pat. No. 5,891,097 discloses an electrochemically driven drug dispenser based on electrolysis of water. In this dispenser, water is contained in an electrochemical cell in which porous metal electrodes are joined to both sides of a solid polymer cation exchange membrane, and both the two electrodes are made to contact with water so as to use oxygen or hydrogen generated from an anode or cathode respectively, upon current conduction. Thus, hydrogen, oxygen, or a gas mixture of hydrogen and oxygen, generated by electrolysis of water when a DC current is made to flow between the electrodes, is used as a pressurization source of the drug dispenser.

Electrochemical oxygen and hydrogen pumps are constructed in a similar way to the above discussed water electrolysis cell and are described in several United States patents, including U.S. Pat. Nos. 5,938,640, 4,902,278, 4,886,514, and 4,522,698. Electrochemically driven fluid dispensers disclosed in these patents have an electrochemical cell in which porous gas diffusion electrodes are joined respectively to the opposite surfaces of an ion exchange membrane containing water functioning as an electrolyte. The electrochemically driven fluid dispenser uses such a phenomenon that when hydrogen is supplied to an anode of the electrochemical cell and a DC current is made to flow between the anode and the cathode, the hydrogen becomes hydrogen ions at the anode. When the produced hydrogen ions reach the cathode through the ion exchange membrane, an electrochemical reaction arises to generate gaseous hydrogen thereat. Since the net effect of these processes is transport of hydrogen from one side of the membrane to the other, this cell is also called hydrogen pump. The hydrogen generated and pressurized at the cathode is used as a driving source for pushing a piston, a diaphragm, or the like.

Alternatively, oxygen may be used in place of hydrogen as a reactant in this type of electrochemical cell, wherein the cell then act as an oxygen pump. Thus, oxygen is reduced on one side of a water-containing electrolytic cell and water is oxidized on the opposite side to generate molecular oxygen, with the molecular oxygen so generated being used as the propellant to force liquid from an adjacent reservoir. A variety of different types of devices have been developed and patented.

Gas generating electrolytic cells based on use of electrolytically decomposable chemical compound which produces a reduced metal at the cathode, and generates gaseous oxygen by water oxidation at the anode are disclosed in U.S. Pat. No. 5,744,014. The cell generally includes a graphite anode, an aqueous electrolyte, and a copper hydroxide cathode. As electrical current passes through a circuit in which the cell is connected, copper is plated out in the cathode, and oxygen is released at the anode. To ensure storage stability, an active cathode material is selected such that the cells require an applied voltage for the electrochemical reactions to proceed.

A battery cell is provided in the circuit to drive the current through the gas-generating cell. The rate of oxygen generated at the anode is directly proportional to the current, and acts as a pressurizing agent to perform the work of expelling a fluid from a bladder or other fluid-containing reservoir which has a movable wall which is acted upon as the gas is generated.

While the above-identified electrochemically driven fluid delivery devices are operable for certain applications, they are not optimal for others. In particular, the above-identified fluid delivery devices are based on gas generation, and are suitable for fluid delivery at rates greater than about 20 microliters per day. However, for delivery of very small drug volumes such as about 100 microliters over an extended period of time, and especially for implantable devices, gas generation is not a suitable method for drug delivery. Another problem is that gas generating pumps are sensitive to temperature and atmospheric pressure. For this purpose, osmotic and electroosmotic pumps are more appropriate.

An osmotic pump involves imbibing water or another driving fluid. The pump consists of three chambers: a salt chamber, a water chamber, and a drug chamber. The salt and water chambers are separated by a semi-permeable membrane. This membrane is permeable to water but impermeable to salt. The drug chamber is separated from the other two by a flexible diaphragm. Water imbibes osmotically into the salt chamber creating hydrostatic pressure, which in turn exerts a force on the diaphragm—thus expelling the fluid. The use of osmotic pumps is typically limited to application requiring constant fluid delivery. In order to vary the fluid flow, it is typically necessary to provide numerous osmotic pumps with differing outputs. These limitations make it inconvenient for the patient to use and control such devices. Osmotic pumps also require charging, (the time required for liquid to diffuse through the semi-permeable membrane and begin dissolving the osmagent at steady state) which delays delivery of the medicament, and further limits their suitability for instantaneous or emergency use.

An electroosmotic pump pumps a fluid susceptible to electroosmotic transport. Electroosmotic pump is an electrolytic cell having a permselective ion exchange membrane and therefore it requires an external DC power source to drive the electrode reactions. U.S. Pat. No. 3,923,426 discloses an electrochemically driven fluid dispenser based on electroosmotic fluid transport. The pump comprises a plastic housing having a fluid inlet and outlet, a pair of spaced silver-silver chloride electrodes disposed in the housing and connected to a D.C. power source, a porous ceramic plug which has a high zeta potential relative to the fluid, a cation exchange membrane positioned on each side of the ceramic plug between it and the electrode facing it and passageway in the housing extended from the fluid inlet to one side of the plug and from the other side of the plug to the outlet. When a potential difference is applied across anode and cathode the transport fluid will flow through porous plug in the direction from anode to cathode. This pump is suitable for fluid delivery at rates greater than about 20 microliters per day. The main disadvantage of such electroosmotic pumps with a porous plug is that the delivery pressures are very low, well below 0.5 ATM. In addition, any ions in the driving fluid will substantially effect the zeta potential and reduce the electro-osmotic flow.

Accordingly, there has been a need for a volume efficient fluid dispenser where the delivery mechanism occupies a part of the overall device, that is portable, can be miniaturized and therefore implanted, and is highly accurate in the delivering small volumes of fluid with precision and accuracy, that can be programmed at will to change the release rate.

SUMMARY OF THE INVENTION

The present invention is directed to a fluid delivery device, comprising: (a) an electrochemical pump, wherein the pump is capable of transporting water; (b) a pump product chamber, wherein the pump product chamber is capable of retaining water generated from the pump; (c) a displaceable member positioned between the pump product chamber and a reservoir, wherein the displaceable member is controllably displaced upon generation of water from the electrochemical pump; (d) a reservoir, wherein the reservoir is capable of containing a fluid which is delivered upon displacement of the displaceable member; and (e) a housing for containing the pump, the pump product chamber, the displaceable member, and the reservoir.

In a preferred embodiment of the present invention, the pump engine comprises a protective porous separator, a first electrode, a second electrode, an ion exchange membrane, and an electric resistor. In this embodiment, the pump may further include an activation switch and a support member(s).

Preferably, the displaceable member is selected from the group consisting of a piston, bladder, diaphragm, plunger, and mixtures thereof.

In yet another aspect of the present invention, the reservoir includes one or more apertures and contains a fluid selected from the group consisting of a medicament, lubricant, fragrant fluid, chemical agent, and mixtures thereof.

The present invention is also directed to a process for delivering a fluid, comprising the steps of: (a) providing a fluid delivery device having an electrochemical water transporting pump; (b) transporting water through the water transporting pump; thereby expanding a volume of a pump product chamber; (c) generating pressure from the expanded pump product chamber; and (d) displacing a displaceable member, and, in turn, controllably expelling fluid from the fluid delivery device.

BRIEF DESCRIPTION OF THE DRAWINGS

The invention will now be described with reference to the drawings wherein.

DETAILED DESCRIPTION OF THE INVENTION

Figure 1:
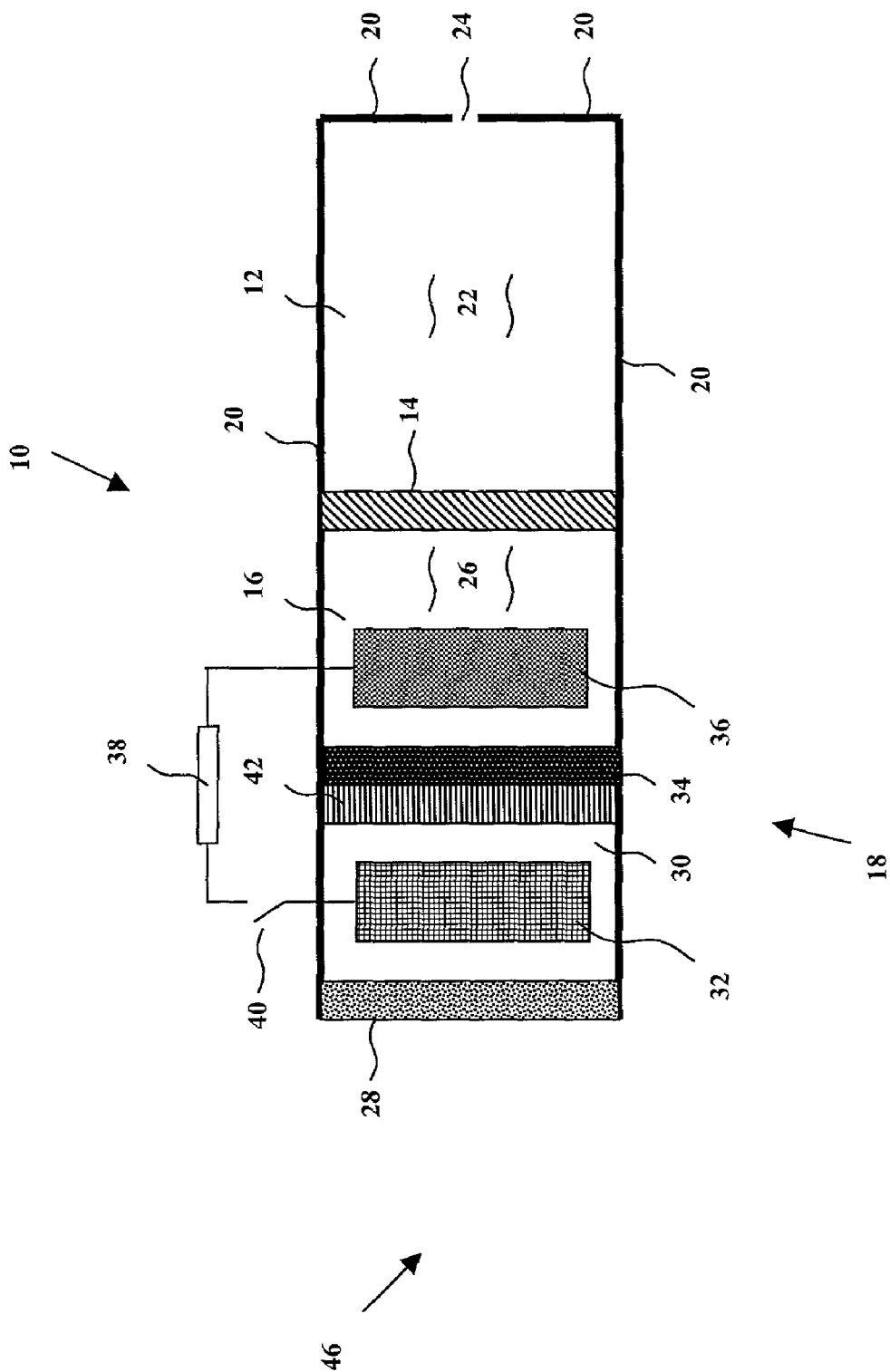
FIG. 1 of the drawings is a cross-sectional schematic representation of a fluid delivery device having an anionic exchange membrane fabricated in accordance with the present invention.

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings with like reference characters.

Referring now to the drawings and to FIG. 1 in particular, a first embodiment of fluid delivery device 10 is shown, which generally comprises reservoir 12, displaceable member 14, electrochemical pump product chamber 16, electrochemical pump 18, and housing 20. It will be understood that the term "fluid" is herein defined as a liquid, gel, paste, or other semi-solid state material that is capable of being delivered out of a reservoir. It will be further understood that FIG. 1 is merely a schematic representation of fluid delivery device 10. As such, some of the components have been distorted from their actual scale for pictorial clarity.

Reservoir 12 is capable of containing fluid 22, such as a medicament, lubricant, fragrant fluid, chemical agent, or mixtures thereof, which is/are delivered upon displacement of displaceable member 14. Reservoir 12 may include one or more apertures 24 for directing delivery of fluid 22 from fluid delivery device 10. Reservoir 12 may be fabricated from any one of a number of materials, including metals, glass, natural and synthetic plastics, composites—just to name a few.

Displaceable member 14 is positioned between reservoir 12 and electrochemical pump product chamber 16. Displaceable member 14 is shown in FIG. 1, for illustrative purposes only, as comprising a piston, however, other displaceable members that would be known to those having ordinary skill in the art having the present disclosure before them are likewise contemplated for use, including a bladder, diaphragm, plunger, etceteras.

Electrochemical pump product chamber 16 is positioned between displaceable member 14 and electrochemical pump 18, and is capable of containing water 26 that, as will be discussed in greater detail below, is controllably generated during operation of electrochemical pump 18. Similar to reservoir 12, electrochemical pump product chamber 16 may be fabricated from any one of a number of materials, including metals, glass, natural and synthetic plastics, composites—just to name a few.

For purposes of the present disclosure electrochemical pump 18 is shown in FIG. 1 as including protective porous separator 28, auxiliary electrode compartment 30, auxiliary electrode 32, anion exchange membrane 34, active electrode 36, electric resistor 38, and activation switch 40, and support members 42.

Protective porous separator 28 is positioned at an end of fluid delivery device distal from reservoir 12. Protective porous separator 28 is generally permeable to $H_2O$ molecules, and in cooperation with salt solution from auxiliary electrode compartment 30, (e.g. metal halides, such as NaCl), enables water from external source 46 (e.g. an inside of a living being's body) to diffuse or migrate into auxiliary electrode compartment 30. Protective porous separator 28 may be fabricated from any one of a number of materials, including metals, glass, natural and synthetic plastics, composites—just to name a few. It will be understood that the use of a separator is not necessarily required and, accordingly, when not used, auxiliary electrode 32 can be exposed directly to fluid, if desired.

Auxiliary electrode 32, anionic exchange membrane 34, and active electrode 36 are respectively positioned adjacent protective porous separator 28. Auxiliary electrodes 32 is a porous cathode pellet that can be readily reduced when is coupled with active metal anode 36. Auxiliary electrode 32 may be fabricated from porous silver chloride, manganese dioxide or other materials that can be readily reduced or may catalyze reduction reaction (e.g. reduction of oxygen or evolution of gaseous hydrogen from water) when is coupled with active metal anode. Active metal anode 36 is a solid pellet, mesh or metal powder type electrode fabricated from, for example, zinc, iron, magnesium, aluminum or other corrosion stable metal and alloys. Although not shown, auxiliary electrode 32 may include conventional current collector, such as screen, mesh or wire current collectors fabricated from, for example, silver, titanium, platinum, or other corrosion stable metals, Active metal anode 36 also may include conventional current collector, such as screen, mesh or wire current collectors fabricated from the same metal as that of the active anode or it may be fabricated from other metals such as, for example, brass which is coated with the same metal as is the active anode metal. While specific examples of electrode materials and current collectors have been disclosed, for illustrative purposes, it will be understood that other electrode materials known to those with ordinary skill in the art having the present disclosure before them are likewise contemplated for use.

Ion exchange membrane 34 is positioned between first electrode 32 and second electrode 36, and is an anionic exchange membrane. The anion exchange materials from which the membrane 34 may be made are well known in the art and do not require extensive elaboration. In brief these materials are cross-linked polymer resins of the strong base type. Preferred resins are the copolymers of styrene and divinyl benzene having quaternary ammonium ion as the charge group, which have a high selectivity for chloride ions and high resistance to organic fouling. Such anionic membranes are, for example, Neosepta type membranes, which are commercially available from AMERIDIA (www.ameridia.com).

Electric resistor 38 is connected to the electrodes via conventional electrical conduit and, as will be discussed in greater detail below, directly controls the rate of water transfer from external source 46 to electrical pump product chamber 16.

Support members 42 are highly porous solid disk materials that provide mechanical rigidity for the ion exchange membrane, and allow water to transport through it. They can be made of hard plastics, ceramics, glass or corrosion stable metals (e.g. titanium), or a combination thereof.

In operation, fluid delivery device 10 can deliver fluid 22 in accordance with the following process. Initially, activation switch 40 is actuated, whereupon an electrical circuit is complete which causes electrode reactions to take place at the electrodes 32 and 36, and water to be extracted from external environment 46, and, ultimately to be driven across ion exchange membrane 34 into electrical pump product chamber 16. Thus, water from external environment, such as a human body diffuses through protective porous separator 28 into the first electrode compartment 30. (Of course, when the separator is not used, fluid will come directly in contact with the first electrode). When the first electrode 32 is made of silver chloride and the second electrode 36 is made of zinc, the following reactions take place. At first electrode silver chloride is reduced to metallic silver releasing chloride ions into solution according to the equation:

$$2AgCl + 2e^- \rightarrow 2Ag + 2Cl^- \quad (1)$$

Chloride ions thus formed are dissolved in water and migrate under the influence of the electric field through ion exchange membrane 34 towards second electrode 36 in electrical pump product chamber 16. At second electrode 36 zinc is dissolved according to the equation:

$$Zn \rightarrow Zn^{2+} + 2e^- \quad (2)$$

Zinc ions thus formed react with incoming chloride ions forming zinc chloride according to the equation:

$$Zn^{2+} + 2Cl^- \rightarrow ZnCl_2 \quad (3)$$

In addition to the electrochemical formation of zinc chloride according to the equation (3), during passage of the chloride ions through the membrane, water is entrained with chloride ions so that at the opposite side of the membrane additional amount of water is produced. This water transport is known in the art as electroosmotic transport. Since the anionic membrane is selective for anions this means that only anions can pass through the membrane. Therefore, water may be transported through the membrane only in one direction. The formed zinc chloride and water molecules generate pressure within the electrochemical pump product chamber 16. The generated pressure, in turn, imparts a force upon displaceable member 14—the only movable component. Displaceable member 14 is displaced laterally away from electrochemical pump product chamber 16, which controllably expels fluid from reservoir 12. It will be understood that the above-identified device and process enables a controlled delivery of a fluid over an extended period of time at a relatively precise and accurate rate inasmuch as the water transported is proportional to the current, which in turn depends on the value of resistor 38. It will be understood, therefore, that the fluid delivery rate is controlled by selection of the resistor and not by the rate at which water is permitted to enter the housing via convection action of protective porous separator 28.

Figure 2:
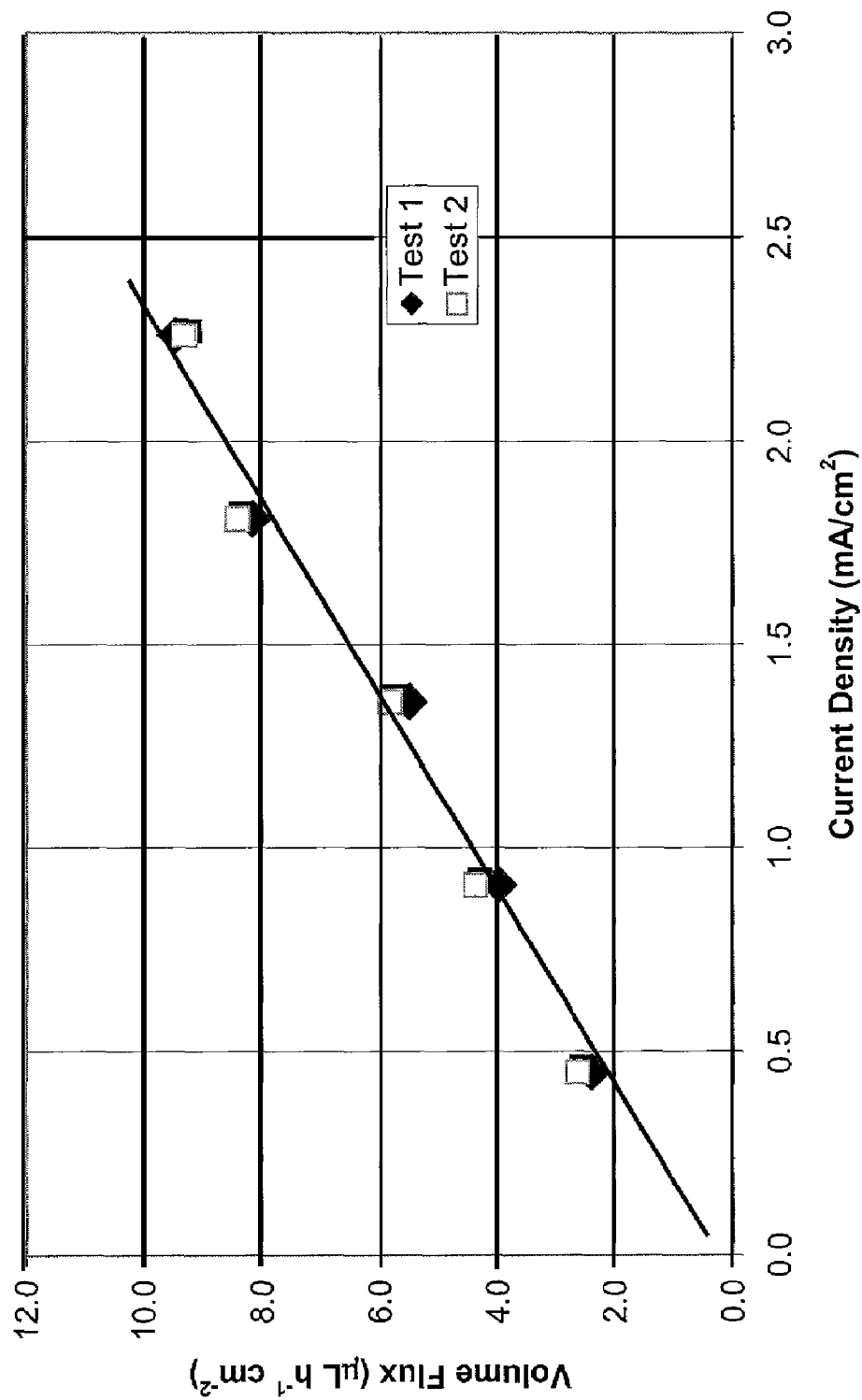
FIG. 2 is a graph of volume flux versus current density in the volume flax range from 2.0 to 10.0 $\mu L\ h^{-1}\ cm^{-2}$ for a fluid delivery device having an anionic exchange membrane fabricated in accordance with the present invention. Cell parameters: AMI 7001 ion exchange membrane, powder zinc anode, nickel mesh cathode, 0.9% NaCl electrolyte.
Figure 3:
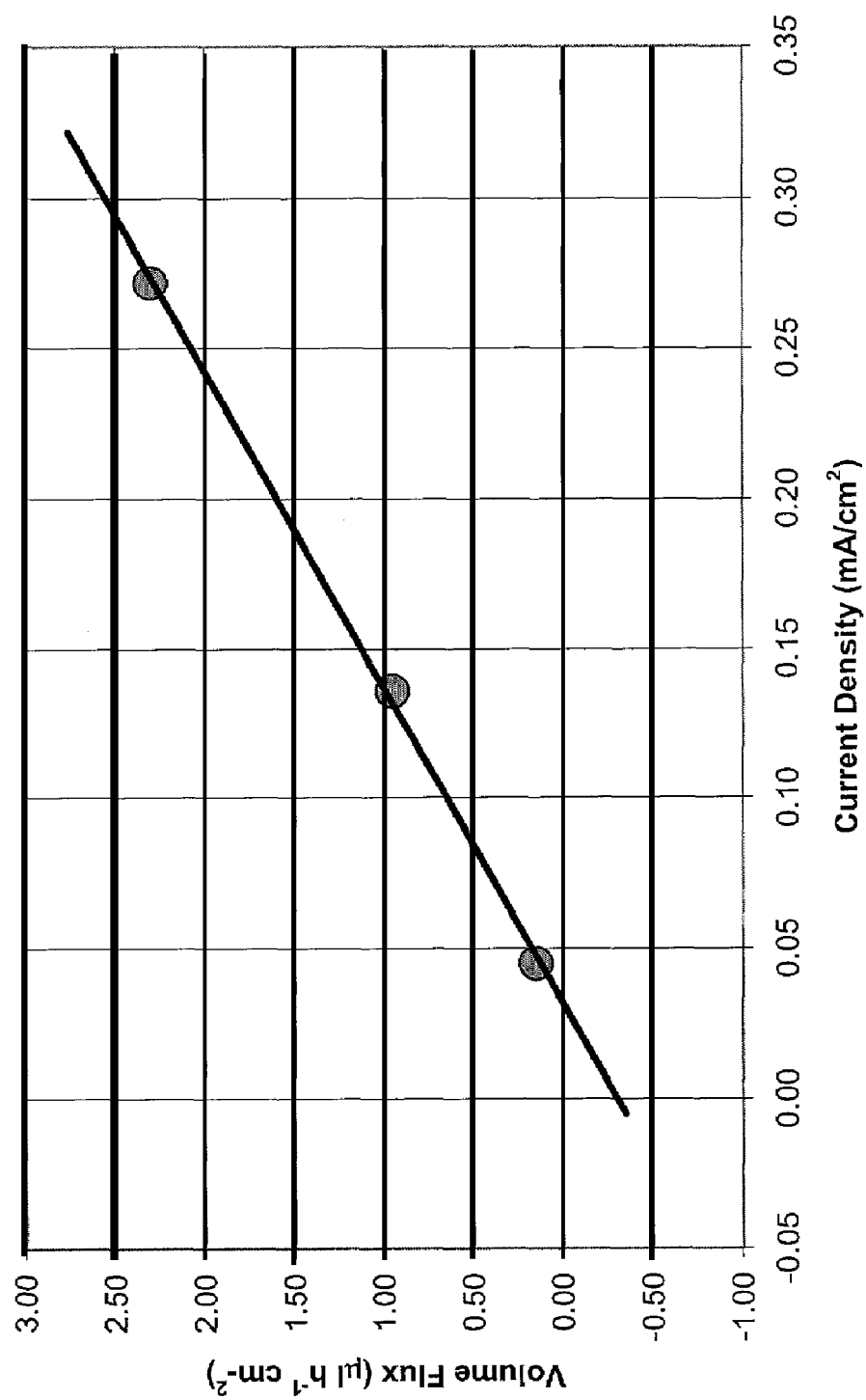
FIG. 3 is a graph of volume flux versus current density in the volume flax range from 0 to 2.5 $\mu L\ h^{-1}\ cm^{-2}$ for a fluid delivery device having an anionic exchange membrane fabricated in accordance with the present invention. Cell parameters: Neosepta® AFN ion exchange membrane, solid zinc anode, silver chloride cathode, 0.9% NaCl electrolyte.
Figure 4:
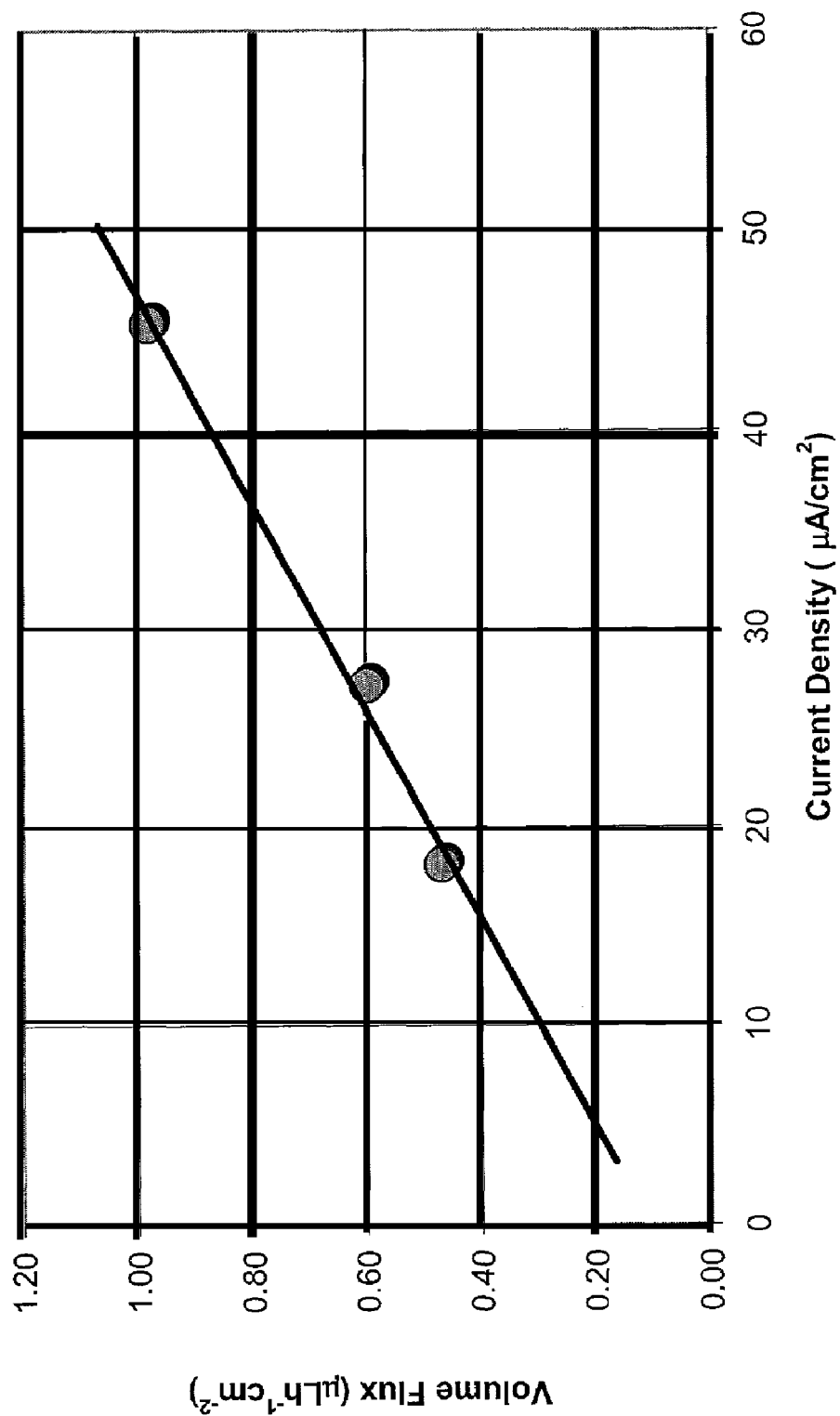
FIG. 4 is a graph of volume flux versus current density in the volume flax range from 0.5 to 2.5 $\mu L\ h^{-1}\ cm^{-2}$ for a fluid delivery device having an anionic exchange membrane fabricated in accordance with the present invention. Cell parameters: Neosepta® AMX ion exchange membrane, solid zinc anode, silver chloride cathode, 0.9% NaCl electrolyte.

For an embodiment such as the one illustrated in the drawings a linear relationship between volume flux and current density was obtained at high and low volume fluxes. This is illustrated in FIG. 2 for volume flux ranging from 2.0 to 10.0 $\mu L\, h^{-1}\, cm^{-2}$ and in FIG. 3 for volume flux ranging from 0.1 to 2.5 $\mu L\, h^{-1}\, cm^{-2}$. The current density required to produce such volume fluxes depends very much on the membrane type used and may be as low as 20 $\mu A\, cm^{-2}$ to produce a volume flux of 0.5 $\mu L\, h^{-4}\, cm^{-2}$, as shown in FIG. 4. Another feature of the embodiment shown in FIG. 1 is high stability operation over more than 1000 hours of operation.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A fluid delivery device, comprising:
   an electrochemical pump comprising a first electrode, a second electrode, and an anion exchange membrane positioned therebetween, at least one of said electrodes spaced from said anion exchange membrane, wherein the electrochemical pump is capable of transporting water;
   an electrochemical pump product chamber, wherein the electrochemical pump product chamber is capable of retaining water transported by the electrochemical pump;
   a displaceable member positioned between the electrochemical pump product chamber and a reservoir, wherein the displaceable member is controllably displaced upon transportation of water from the electrical pump;
   a reservoir, wherein the reservoir is capable of containing a fluid which is delivered upon displacement of the displaceable member; and
   a housing for containing the electrochemical pump, the electrochemical pump product chamber, the displaceable member, and the reservoir, said housing configured to allow fluid external to said housing to operably communicate with at least one of said electrodes.

2. The fluid delivery device according to claim 1, wherein the electrochemical pump farther comprises a protective porous separator and an electric resistor.

3. The fluid delivery device according to claim 2, wherein the electrochemical pump further includes an activation switch, and a support member.

4. The fluid delivery device according to claim 2, wherein the protective porous separator is generally permeable to $H_2O$ molecules.

5. The fluid delivery device according to claim 2, wherein the first and second electrodes form a galvanic couple.

6. The fluid delivery device according to claim 1, wherein the displaceable member is selected from the group consisting of a piston, bladder, diaphragm, plunger, and mixtures thereof.

7. The fluid delivery device according to claim 1, wherein the reservoir contains a fluid selected from the group consisting of a medicament, lubricant, fragrant fluid, chemical agent, and mixtures thereof.

8. The fluid delivery device according to claim 1, wherein the reservoir includes one or more apertures.

9. A fluid delivery device, comprising:
   an electrochemical pump, wherein the electrochemical pump is capable of transporting water, and wherein the electrochemical pump includes a protective porous separator, a first electrode, a second electrode, an anion exchange membrane, and an electric resistor;
   an electrochemical pump product chamber, wherein the electrochemical pump product chamber is capable of retaining water transported from the electrochemical pump;
   a displaceable member positioned between the electrochemical pump product chamber and a reservoir, wherein the displaceable member is controllably displaced upon transportation of water from the electrical pump;
   a reservoir, wherein the reservoir is capable of containing a fluid which is delivered upon displacement of the displaceable member; and
   a housing for containing the electrochemical pump, the electrochemical pump product chamber, the displaceable member, and the reservoir, said housing configured to allow fluid external to said housing to operably communicate with at least one of said electrodes.

10. The fluid delivery device according to claim 9, wherein the electrochemical pump further includes an activation switch, and a support member.

11. The fluid delivery device according to claim 9, wherein the protective porous separator is generally permeable to $H_2O$ molecules.

12. The fluid delivery device according to claim 9, wherein the first and second electrodes form galvanic couple.

13. The fluid delivery device according to claim 9, wherein the displaceable member is selected from the group consisting of a piston, bladder, diaphragm, plunger, and mixtures thereof.

14. The fluid delivery device according to claim 9, wherein the reservoir contains a fluid selected from the group consisting of a medicament, lubricant, fragrant fluid, chemical agent, and mixtures thereof.

15. The fluid delivery device according to claim 9, wherein the reservoir includes one or more apertures.

16. A fluid delivery device, comprising:
an electrochemical pump, wherein the electrochemical pump is capable of transporting water, and wherein the electrochemical pump comprises:
    a protective porous separator positioned at an end of the fluid delivery device;
    a first electrode compartment which emanates contiguously from the a protective porous separator;
    a first electrode residing within the first electrode compartment;
    an anion exchange membrane which emanates contiguously from the first electrode compartment;
    a second electrode compartment which emanates contiguously from the anion exchange membrane opposite the first electrode compartment;
    a second electrode residing within the second electrode compartment; and
    an electric resistor which is in electrical communication with the first and second electrodes;
an electrochemical pump product chamber, wherein the electrochemical pump product chamber is capable of retaining water transported from the electrochemical pump;
a displaceable member positioned between the electrochemical pump product chamber and a reservoir, wherein the displaceable member is controllably displaced upon transportation of water from the electrochemical pump;
a reservoir, wherein the reservoir is capable of containing a fluid which is delivered upon displacement of the displaceable member; and
a housing for containing the electrochemical pump, the electrochemical pump product chamber, the displaceable member, and the reservoir, said housing configured to allow fluid external to said housing to operably communicate with at least one of said electrodes.

17. The fluid delivery device according to claim 16, wherein the electrochemical pump further includes an activation switch, and a support member.

18. The fluid delivery device according to claim 16, wherein the protective porous separator is generally permeable to $H_2O$ molecules.

19. The fluid delivery device according to claim 16, wherein the first and second electrodes form a galvanic couple.

20. The fluid delivery device according to claim 16, wherein the displaceable member is selected from the group consisting of a piston, bladder, diaphragm, plunger, and mixtures thereof.

21. The fluid delivery device according to claim 16, wherein the reservoir contains a fluid selected from the group consisting of a medicament, lubricant, fragrant fluid, chemical agent, and mixtures thereof.

22. The fluid delivery device according to claim 16, wherein the reservoir includes one or more apertures.

23. The fluid delivery device according to claim 2, wherein the porous separator is not in contact with an electrode.

24. The fluid delivery device according to claim 3, wherein the support member is not an electrode.

25. The fluid delivery device according to claim 1, wherein at least one electrode is substantially nonporous.

26. The fluid delivery device according to claim 25, wherein the substantially nonporous electrode is a solid pellet.

27. The fluid delivery device according to claim 1, further comprising a water source external to said housing.

28. The fluid delivery device according to claim 9, wherein at least one electrode is not in physical contact with said anion exchange membrane.

29. A fluid delivery device, comprising:
an electrochemical pump comprising a first electrode, a second electrode, and an ion exchange membrane positioned therebetween, at least one of said electrodes spaced from said ion exchange membrane, wherein the electrochemical pump is capable of transporting water and wherein said first and second electrodes do not participate in an oxygen-generating reaction;
an electrochemical pump product chamber, wherein the electrochemical pump product chamber is capable of retaining water transported by the electrochemical pump;
a displaceable member positioned between the electrochemical pump product chamber and a reservoir, wherein the displaceable member is controllably displaced upon transportation of water from the electrical pump;
a reservoir, wherein the reservoir is capable of containing a fluid which is delivered upon displacement of the displaceable member; and
a housing for containing the electrochemical pump, the electrochemical pump product chamber, the displaceable member, and the reservoir, said housing configured to allow fluid external to said housing to operably communicate with at least one of said electrodes.

30. The fluid delivery device according to claim 29, further comprising a protective porous separator that is permeable to $H_2O$ molecules.

31. The fluid delivery device according to claim 29, wherein the first and second electrodes form a galvanic couple.

32. The fluid delivery device according to claim 29, wherein the ion exchange membrane is an anionic exchange type membrane.

* * * * *